US00PP32124P2

(12) United States Plant Patent
Van Swieten

(10) Patent No.: US PP32,124 P2
(45) Date of Patent: Aug. 25, 2020

(54) ***PHALAENOPSIS* ORCHID PLANT NAMED 'PHALGETCHA'**

(50) Latin Name: ***Phalaenopsis* hybrid**
Varietal Denomination: PHALGETCHA

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/602,634

(22) Filed: Nov. 12, 2019

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ... A01H 5/02; A01H 5/00; A01H 5/08; A01H 6/62
See application file for complete search history.

*Primary Examiner* — June Hwu
(74) *Attorney, Agent, or Firm* — Jondle & Associates, P.C.

(57) ABSTRACT

A new and distinct variety of *Phalaenopsis* plant named 'PHALGETCHA', particularly characterized by having large white flowers, 1 to 2 peduncles that are long and sturdy, and is propagated by meristem tissue culture, is disclosed.

3 Drawing Sheets

Genus and species: *Phalaenopsis* hybrid.
Variety denomination: 'PHALGETCHA'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGETCHA'.

The new *Phalaenopsis* plant is a product of a planned breeding program conducted by the inventor in Bleiswijk, the Netherlands. The objective of this breeding program was to create a new *Phalaenopsis* plant with numerous attractive and unique white flowers with green-white lips, suitable for potted plant production.

The new *Phalaenopsis* plant 'PHALGETCHA' is a result of cross-pollination made by the inventor in May 2010 in Bleiswijk, the Netherlands, of the proprietary female, or seed parent, *Phalaenopsis* hybrid '00001-1958' (unpatented) with the proprietary male, or pollen parent, *Phalaenopsis* hybrid '00001-1988' (unpatented).

The new *Phalaenopsis* was selected by the inventor as a single plant within the progeny of the stated cross-pollination in a controlled greenhouse in Bleiswijk, the Netherlands, in April 2013. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 16, 2019, by Applicant who obtained the subject matter disclosed directly from the inventor. 'PHALGETCHA' has not been made publicly available or sold anywhere in the world prior to the effective filing date of this application with the exception of sales or disclosures made one year or less before the effective filing date of this claimed invention by Applicant who obtained 'PHALGETCHA' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALGETCHA' as a new and distinct variety of *Phalaenopsis* plant:

1) Large white flowers;
2) 1 to 2 peduncles; and
3) Peduncle is long and sturdy.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, the Netherlands, from 50-week-old plants in July 2019. Colors in the photographs may differ from the color values cited in the detailed botanical description, which accurately describe the actual colors of the new variety.

DESCRIPTION OF THE NEW VARIETY

Figure 1:
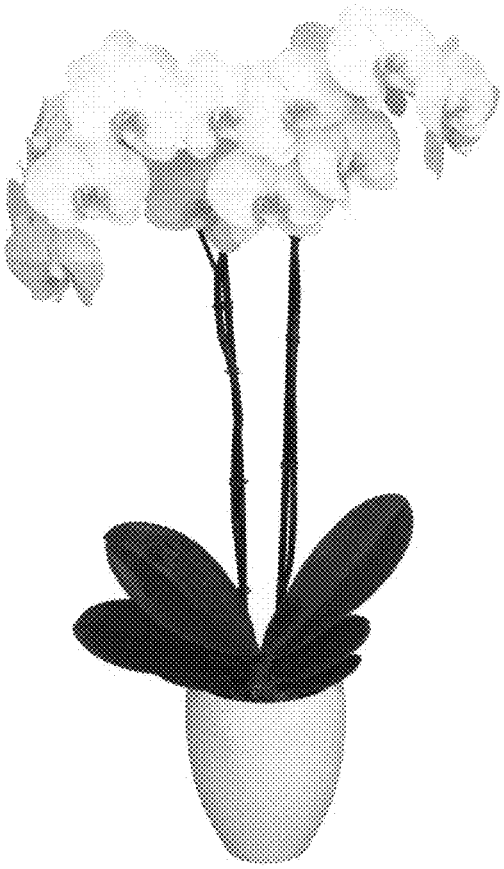
FIG. 1 shows the overall plant habit, including blooms and foliage of 'PHALGETCHA'.
Figure 2:
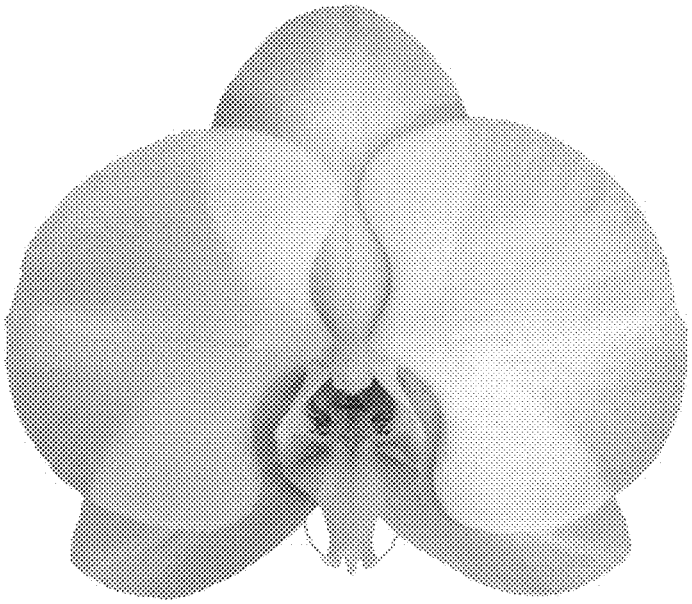
FIG. 2 shows a close-up of a flower of 'PHALGETCHA'.
Figure 3:
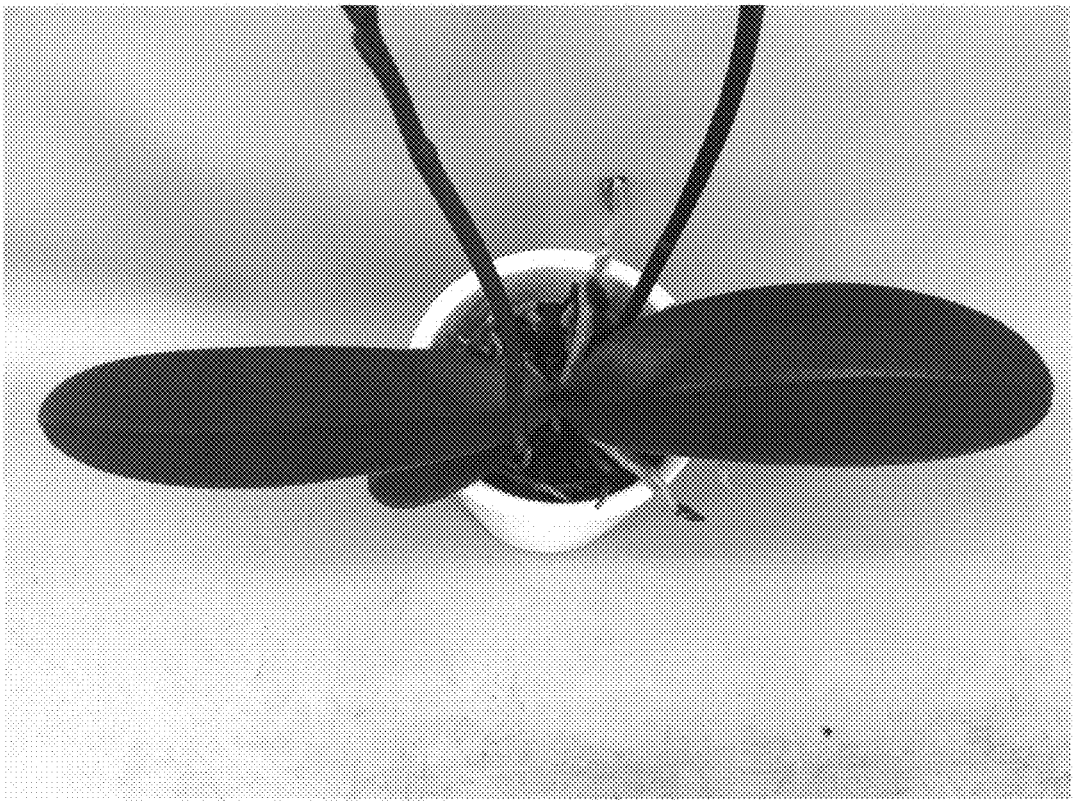
FIG. 3 shows an overhead view of the leaves of 'PHALGETCHA'.

The following detailed description sets forth the distinctive characteristics of 'PHALGETCHA'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in July 2019 on flowering plants which were planted in 12-centimeter (diameter) pots. After in-vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGETCHA'.

Parentage:

*Female parent*.—*Phalaenopsis* cultivar '00001-1958' (unpatented).

*Male parent*.—*Phalaenopsis* cultivar '00001-1988' (unpatented).

Propagation:

*Type*.—Meristem tissue culture.

Roots:

*Root description*.—Greyed-green (between RHS 190B and 190C) colored roots with branching lateral roots having light yellow-green (RHS 145B) colored root tips.

Plant:

*Commercial crop time to flowering*.—Following asexual propagation (in-vitro), the rooted cuttings grow for 20-24 weeks. After transplantation into 12-cm pots, the plants are finished after 48 to 50 weeks.

*Growth habit of peduncle*.—Upright to slightly pendant with raceme inflorescence.

*Height (from soil level to top of inflorescence)*.—Approximately 60.0 cm to 70.0 cm.

*Width (measured from leaf tips)*.—About 35.0 cm to 40.0 cm.

*Vigor*.—Strong.

Leaves:

*Mature leaves*.—Quantity per plant: 8 to 10 leaves are produced before flowering. Length (fully expanded): 20.0 cm to 25.0 cm. Width: 7.0 cm to 8.0 cm. Position of the broadest part of the leaf: Toward the apex. Shape: Oblong. Base shape: Moderately elongated. Apex: Acute unequal. Leaf blade angle with the petiole (measured from the horizontal position): Between 20 degrees and 30 degrees. Leaf margin: Entire. Color: Upper surface: RHS 146A. Lower surface: RHS 146A. Texture (both upper and lower surfaces): Smooth. Thickness: 2.1 mm to 2.3 mm. Variegation: Absent. Venation: Pattern: Parallel. Color of the midvein: Upper surface: RHS 146B. Lower surface: RHS 146B.

Peduncle:

*Quantity per plant*.—1 to 2.

*Number of flowers per peduncle*.—8 to 10.

*Length*.—70.0 cm to 80.0 cm.

*Diameter*.—6.3 mm to 6.6 mm.

*Strength*.—Strong.

*Aspect*.—Upright to slightly pendant.

*Texture*.—Smooth.

*Color*.—Mix of brown (RHS N200A) and green (RHS 137A).

*Internode length*.—4.0 cm to 5.0 cm.

Inflorescence description:

*Appearance*.—Upright to slightly pendant, raceme inflorescence with bilaterally symmetrical flowers that open in succession beginning with the lowermost flower.

*Number of inflorescences*.—1 to 2.

*Inflorescence size*.—Height (from base to tip): 250.0 mm to 300.0 mm.

*Flowering time*.—First flowers can be expected 10 to 11 months after planting in a 12-cm pot.

*Flower*.—Height: 100.0 mm to 110.0 mm. Diameter: 120.0 mm to 130.0 mm. Depth of lip: 25.0 mm to 26.0 mm.

*Flower longevity*.—On the plant: 12 to 16 weeks.

*Flower shape*.—Flat.

*Fragrance*.—Absent.

*Flower bud*.—Average size: Large. Length: 30.0 mm to 35.0 mm. Width: 25.0 mm to 28.0 mm. Shape: Egg shaped. Color: Light green (RHS 145C).

*Petals*.—Arrangement: Open/free. Shape: Semi-circular. Apex: Rounded with a slight emargination. Margin: Entire. Length (from base to tip): 75.0 mm to 80.0 mm. Width: 60.0 mm to 65.0 mm. Position of the broadest part of the petal: Toward the base. Color (when fully opened): Upper surface: Basic color: RHS NN155C. Over color: Absent. Lower surface: Basic color: RHS NN155C. Over color: Absent. Number of spots and stripes on the petals: None. Color of spots and stipes on the petals: None. Density of netting of the petals: None. Color of the netting: None.

*Dorsal sepal*.—Shape: Elliptic. Apex: Rounded. Margin: Entire. Length (from base to tip): 60.0 mm to 65.0 mm. Width: 45.0 mm to 48.0 mm. Position of the broadest part of the dorsal sepal: In the middle. Color (when fully opened): Upper surface: Basic color: RHS NN155C. Over color: Absent. Lower surface: Basic color: RHS NN155C. Over color: RHS 76D. Number of spots and stripes on the dorsal sepals: None. Color of spots and stripes on the dorsal sepals: None. Density of netting of the dorsal sepals: None. Color of the netting: None.

*Lateral sepals*.—Shape: Ovate. Apex: Obtuse symmetric. Margin: Entire. Length (from base to tip): 60.0 mm to 65.0 mm. Width: 38.0 mm to 40.0 mm. Position of the broadest part of the lateral sepal: In the middle. Color (when fully opened): Upper surface: Basic color: RHS NN155C. Over color: None. Lower surface: Basic color: RHS NN155C. Over color: A hint of green (RHS 138D) at the base. Number of spots and stripes on the lateral sepals: None. Color of spots and stripes on the lateral sepals: None. Density of netting of the lateral sepals: None. Color of the netting: None.

*Labellum* (*lip*).—Whiskers: Present. Length of whiskers: 30.0 mm to 32.0 mm. Color of whiskers: White (RHS NN155C) with yellow tips (RHS 6A). Pubescence on the lip: Absent.

*Lateral lobe*.—Shape: Spatulate. Margin: Entire. Length: 22.0 mm to 24.0 mm. Width: 18.0 mm to 20.0 mm. Color: Upper surface: Few reddish orange stripes (RHS N178B) at the base; white (RHS NN155C) in the center and a yellow edge (RHS 9B) on the front Lower surface: White (RHS NN155C) with yellow (RHS 9B) toward the front. Number of spots and stripes on the lateral lobe: Few. Color of spots and stripes on the lateral lobe: RHS N170A. Density of netting of the lateral lobe: None. Color of the netting: None.

*Apical lobe*.—Shape: Triangular. Margin: Entire. Length: 25.0 mm to 27.0 mm. Width: 25.0 mm to 27.0 mm. Color: Upper surface: White (RHS NN155C) in the center; yellow green RHS 154B at the base; slightly green (RHS N144B) toward the edge; small brownish orange margin (RHS N170A0 towards the callus. Lower surface: A hint of green (RHS N144B) in the middle, turning white (RHS NN155C) becoming slightly green (RHS 144B) at the edge and a small brownish orange margin (RHS N170A) towards the callus. Number of spots and stripes on the apical lobe: None. Color of spots and stripes on the apical lobe: None. Density of netting of the apical lobe: None. Color of the netting: None.

*Callus*.—Average size: Height: 0.7 cm to 0.8 cm. Length: 0.8 cm to 0.9 cm. Width: 0.5 cm to 0.6 cm. Color: Yellow (RHS 13B) with orange spots (RHS 17A).

Reproductive organs:

*Column*.—Length: 9.0 mm to 10.0 mm. Diameter: 7.0 mm. Color: White (RHS NN155C).

*Pollinia*.—Quantity: 2. Diameter: 1.0 mm to 1.1 mm. Color: Orange (RHS 17A).

*Ovary*.—Length: 17.0 mm to 18.0 mm. Diameter: 3.0 mm to 4.0 mm.

*Pedicel*.—Length: 43.0 mm to 44.0 mm. Diameter: 3.0 mm to 4.0 mm. Color: Green (RHS 138B) at the base turning a little pink (RHS 76D) at the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGETCHA' differs from female parent plant '00001-1958' (unpatented) in that 'PHALGETCHA' has shorter whiskers and narrower petals than '00001-1958'.

'PHALGETCHA' differs from male parent plant '00001-1988' (unpatented) in that 'PHALGETCHA' has a moderately elongated leaf base shape, whereas '00001-1988' has a very elongated leaf base shape. Additionally, 'PHALGETCHA' has larger flowers than '00001-1988'.

'PHALGETCHA' is most similar to the commercial *Phalaenopsis* plants named 'PHALFOUDI' (U.S. Plant Pat. No. 29,453) and 'PHALGOPEL' (U.S. Plant Pat. No. 31,515). 'PHALGETCHA' differs from the commercial variety 'PHALFOUDI' in that 'PHALGETCHA' has larger flowers, longer whiskers, and longer dorsal sepals than 'PHALFOUDI'.

'PHALGETCHA' differs from the commercial variety 'PHALGOPEL' in that 'PHALGETCHA' has larger flowers and longer petals than 'PHALGOPEL'.

I claim:

1. A new and distinct variety of *Phalaenopsis* plant named 'PHALGETCHA', substantially as described and illustrated herein.

* * * * *